United States Patent [19]
Gangemi

[11] Patent Number: 4,966,585
[45] Date of Patent: Oct. 30, 1990

[54] INFUSION APPARATUS

[76] Inventor: Ronald J. Gangemi, 10607 Barmer Mine Way, Nevada City, Calif. 95959

[21] Appl. No.: 200,231

[22] Filed: May 31, 1988

[51] Int. Cl.$^5$ .............................................. A61M 37/00
[52] U.S. Cl. ..................................... 604/131; 604/134; 604/135; 604/228
[58] Field of Search ........................... 604/131, 133–9, 604/228-2, 240, 242-3, 30–31, 181, 186, 250, 283

[56] References Cited
U.S. PATENT DOCUMENTS

| | | | |
|---|---|---|---|
| 2,157,503 | 5/1939 | Smith | 604/229 x |
| 2,309,502 | 1/1943 | Douglas | 604/135 |
| 3,880,163 | 4/1975 | Ritterskamp | 604/136 |
| 4,430,080 | 2/1984 | Pasquini et al. | 604/240 |
| 4,623,330 | 11/1986 | Laby et al. | 604/131 X |
| 4,636,197 | 1/1987 | Chu | 604/131 |
| 4,787,406 | 11/1988 | Edwards et al. | 604/250 X |

Primary Examiner—Max Hindenburg
Assistant Examiner—John P. Lacyk
Attorney, Agent, or Firm—John G. Mesaros

[57] ABSTRACT

Apparatus for infusion of a solution into a catheter or the like, the apparatus including a syringe with an administration set having a cup-shaped member configured for selective interlocking engagement with the syringe. The syringe includes a piston member and a coil spring within the bore having a first end urging against the piston. A separable handle member has a shaft axially positionable within the bore, with a reduced diameter threaded end configured for threadably engaging an aperture in the piston. A spring retaining cup within the bore acts against the other end of the spring, with the cup having a central aperture of a dimension sufficient for passage therethrough of the reduced diameter end of the shaft of the handle. Coupling of the handle to the piston compresses the spring via the cup. After filling the syringe, attaching the administration set, and attaching the dispensing fitting to the catheter for the patient, the handle is removed, enabling expansion of the spring, which thus powers the piston to discharge the solution. A controlled flow rate is obtained by providing a fluid flow path of a given or restricted orifice size at the syringe outlet or within the administration set, preferably the latter.

45 Claims, 2 Drawing Sheets

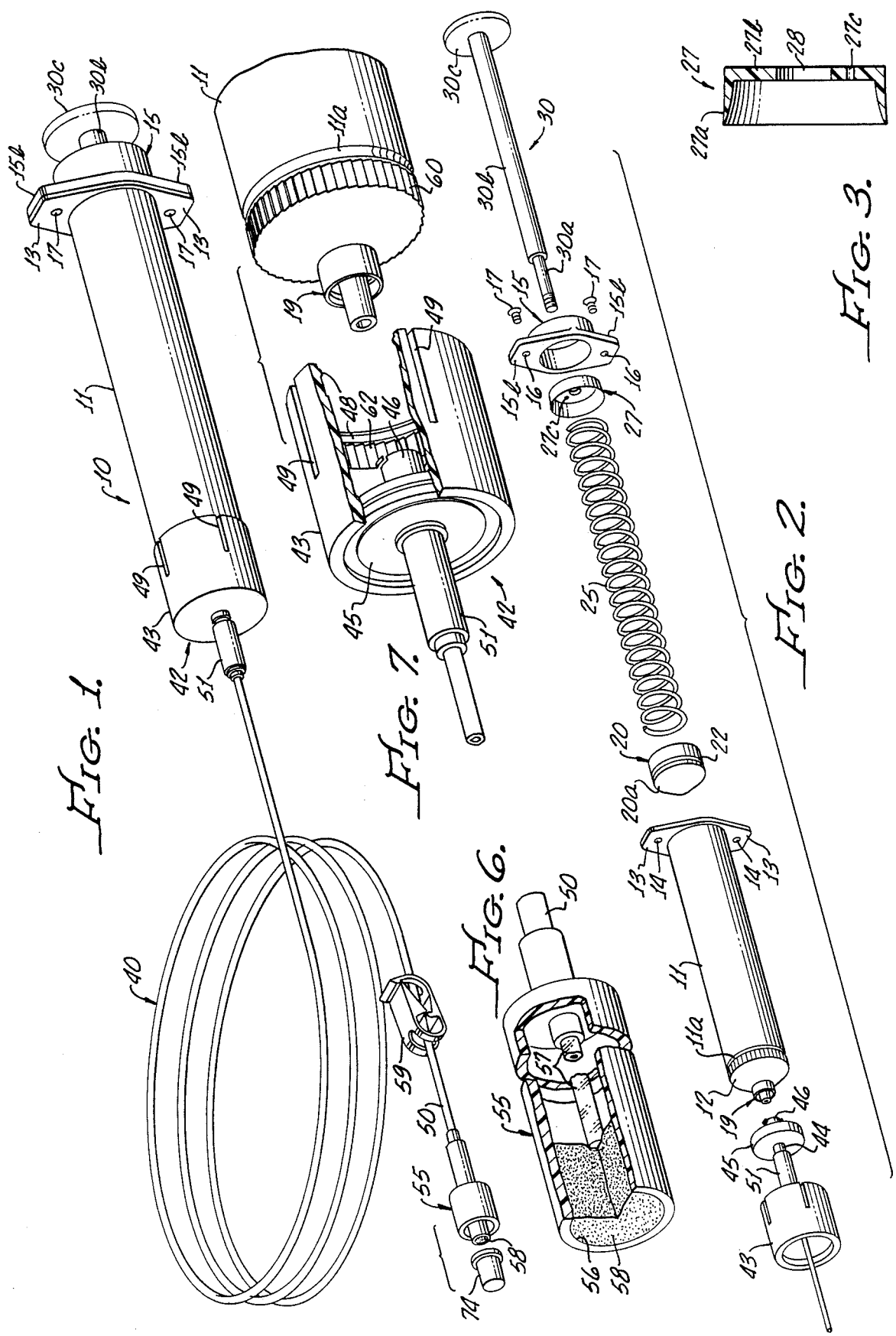

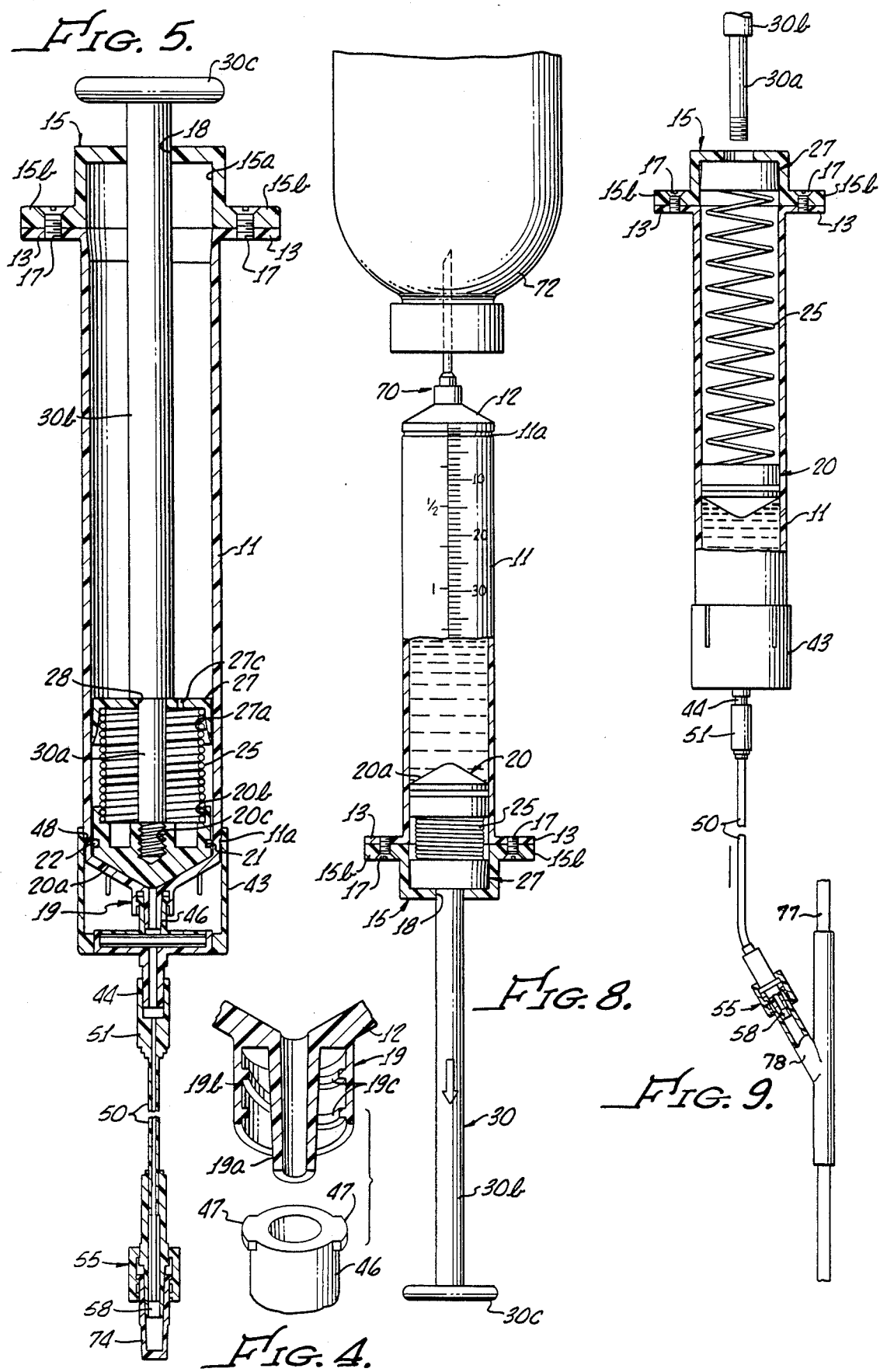

4,966,585

1

INFUSION APPARATUS

BACKGROUND OF THE INVENTION

The background of the invention will be discussed in two parts:

FIELD OF THE INVENTION

This invention relates to infusion apparatus for dispensing solution by a measurable amount, such as milliliters, into a catheter, and more particularly to an infusion apparatus with self-contained power means.

DESCRIPTION OF THE PRIOR ART

In the care and medical treatment of patients, it is oftentimes necessary to inject fluids of various types into the patient, such as for feeding, or for drug and pharmaceutical administration. Infusion apparatus is used to administer drugs and pharmaceutical solutions, usually through an injector site in a catheter.

During the administration of such solutions, dosage is sometimes controlled to flow rates, such as 1 to 20 mls per minute. In some medical infusion devices, elastomeric bladders are used for containing the solution to be administered, with the bladder also serving to provide the force necessary to discharge the solution from the bladder. Such devices are shown and described in U.S. Pat. Nos. 3,469,578; 3,486,539; 3,993,069; 4,201,207; 4,318,400; and 4,386,929.

Other infusion devices, such as one device sold by AVI, Inc./3M, under the mark "Medifuse", utilize a conventional syringe, which is placed in an external device which then powers the syringe to controllably discharge the solution.

In accordance with an aspect of the invention, it is an object of the present invention to provide a new and improved infusion apparatus, which includes a self-contained power source for controllably discharging the solution therefrom.

SUMMARY OF THE INVENTION

The foregoing and other objects of the invention are accomplished by providing an infusion apparatus including a syringe and an administration set, the syringe having a tubular bore with a piston therein threadably coupled to a syringe handle. One end of the syringe has a cap with a central opening and the other end of the syringe is provided with a fitting for receiving tubing or a needle or the like. The syringe handle has a reduced diameter threaded portion and a shaft portion extending axially within the bore, with the other end of the handle passing through the central opening of the cap and terminating exterior to the bore. A power spring encircles the shaft portion of the handle within the bore, with one end of the spring abutting against a surface of the piston. A spring retaining cup member within the bore has the other end of the spring received within the cup, with the outer surface of the closed end in facing relation to the interior of the cap. The closed end of the cup member has a central opening of a diameter sufficient for passage therethrough of the reduced diameter threaded end of the handle. The spring is compressed by insertion of the handle through the central opening of the cap, through the center opening of the cup, with the shoulder between the shaft portion and the threaded portion abutting against the inner surface of the cup to force the spring toward the piston until the threads are engaged to thereby compress the spring.

The administration set includes a cup-shaped member with a filter therein configured for selective locking attachment in liquid flow relation to the dispensing end of the syringe after liquid is drawn therein, with the other end of the tubing including a metering orifice and diffuser member, the size of the orifice controlling the flow rate from the apparatus after the syringe is filled and the handle threadably uncoupled and removed from the syringe, after which the flow of liquid is powered by the force of the spring, and the flow rate controlled by the size of the orifice.

Other objects, features and advantages of the invention will become apparent from a reading of the specification, when taken in conjunction with the drawings, in which like reference numerals refer to like elements in the several views.

BRIEF DESCRIPTION OF THE DRAWINGS

FIG. 1 is a perspective view of the infusion apparatus according to the invention;

FIG. 2 is an exploded perspective view of the syringe and connecting portion of the infusion apparatus of FIG. 1;

FIG. 3 is a cross-sectional view of the spring retaining cup used in the apparatus of FIGS. 1 and 2;

FIG. 4 is an enlarged exploded fragmentary view showing the interconnection between the syringe and the administration set of the apparatus of FIG. 1;

FIG. 5 is a cross-sectional view of the infusion apparatus of FIG. 1;

FIG. 6 is an enlarged perspective view, partially broken away, of the dispensing member of the apparatus of FIG. 1;

FIG. 7 is a perspective view, partially broken away, of an alternate interconnection arrangement for the infusion apparatus according to the invention;

FIG. 8 is a side elevational view, partially in cross-section, of the syringe portion of the infusion apparatus of FIG. 1, with a needle assembly attached, for withdrawing solution from a container; and FIG. 9 is a side elevational view, partially in cross-section, of the infusion apparatus of FIG. 1, with the tubing attached thereto for administering the solution by connection to an injection site of a catheter.

DESCRIPTION OF THE PREFERRED EMBODIMENT

Referring now to the drawings, and particularly to FIG. 1, there is shown infusion apparatus including a syringe, generally designated 10, and a fluid administration set, generally designated 40.

FIG. 2 shows the syringe 10, in exploded perspective view, with a portion of the administration set 40. The syringe 10 includes a tubular generally cylindrical bore 11, with a funnel-shaped integrally formed end 12. The other end of the bore 11 is open and provided with diametrically opposed outwardly extending flanges 13 formed integrally therewith, the flanges including threaded apertures 14. The flanges 13 and apertures 14 are configured for receiving a cap member 15. The cap member 15 has a generally cup-shaped portion 15a of a diameter generally equal to the diameter of the bore 11, and opposing flanges 15b, configured for abutting relation with the flanges 13. The flanges 15b include apertures 16 therethrough positioned for alignment with apertures 14 for receiving screws 17 therethrough for closing the end of bore 11. As shown in FIG. 5, the internal diameter of the cup-shaped portion 15a is generally identical to the internal diameter of the bore 11. The closed end of the portion 15a includes a central opening 18, which lies on the axial centerline of the bore 11 with the cap member 15 assembled to the bore 11.

The funnel-shaped portion 12 of bore 11 has an axial opening in alignment with a fitting 19, which includes an integrally formed external nozzle or spout 19a, with an integrally formed concentric sleeve 19b thereabout (See FIGS. 4 and 5), the interior of the sleeve 19b having a double screw thread, designated 19c, configured therein. The spout 19a is configured for discharge of fluid from within the bore 11 as will be hereinafter described. In spaced relation to the junction of portion 12 with the end of the bore 11, the outer surface of the bore 11 is provided with an annular groove 11a, which together with fitting 19 serves to lock the administration set 40 to the syringe 10.

A piston member 20 is provided for being received within the bore 11, the piston member 20 having a diameter slightly smaller than the interior diameter of the bore 11. The circumference of the piston member 20 is provided with an annular groove 21 for receiving an O-ring 22 therein, and thus providing a fluid-tight seal between the piston member 20 and the interior of bore 11 The nose end 20a of piston member 20 is tapered and configured to the geometrical shape of the interior of the funnel-shaped end 12 of the bore 11 (See FIG. 5).

As shown in FIG. 5, the interior of the piston member 20 is hollowed out to form a cupped portion with a circumferential flange 20b, with the center of the piston member within the hollowed out portion having a centrally disposed threaded aperture 20c. One end of a power compression helical or coil spring 25 is received within this cupped portion, with the spring 25 having a diameter smaller than the internal diameter of bore 11 and sufficient for being received within the cupped portion encircled by the flange 20b. The other end of spring 25 is received within a cupped portion of a spring retaining cup 27 (See also FIG. 3), which has a skirt portion 27a, the interior diameter of which is sufficient for receiving a portion of the spring 25 therein. The closed end 27b of cup 27 is provided with a central opening 28, which opening 28 is axially aligned with opening 18 and of a diameter smaller than the diameter of opening 18. A small relief aperture 27c is provided in the crown of member 27 for facilitating assembly as will be described.

As shown in FIG. 3, the skirt portion 27a has an outwardly extending flare, the outer diameter of which, at the lower end thereof (as viewed in FIG. 5) is slightly greater than the internal diameter of the bore 11. The cup 27 is formed of a suitable plastic or other material with a degree of deformation or elasticity to enable insertion of the cup 27 while providing an interference fit, that is, a measure of frictional resistance, or interference, to sliding movement of cup 27 within bore 11, the purpose of which will be hereinafter explained.

A handle member 30 is provided, the handle member 30 being rod-shaped with a reduced diameter threaded portion 30a, an elongate shaft portion 30b, and an enlarged cap portion 30c. The threaded portion 30a is of a diameter sufficient for being received through the opening 28 of spring retaining cup 27, with the diameter of shaft portion 30b being sufficient for being received through the larger diameter opening 18 of cap member 15.

For assembly of the syringe 10, the piston 20 is inserted into the bore 11, nose end 20a first, with the O-ring 22 thereabout. The spring 25 is then inserted into the bore 11, with the end thereof received within the cupped portion, with the periphery of the end of spring 25 in abutment with the peripheral flange 20b. The cup 27 is then positioned over the spring 25 with the other end of spring 25 within the cup 27, surrounded by the flared skirt 27a, and in abutting relation with the inside of end 27b. The skirt portion 27a is then slightly compressed and inserted within the bore 11, pushing the spring 25 and piston 20 axially toward the funnel-shaped end 12 of bore 11. The relief aperture 27a of cup member 27 permits passage of air from within the bore 11 during insertion of member 27.

The spring 25, in its relaxed, or uncompressed, state, has an axial length which exceeds that of the length of bore 11 to provide the degree of power required. By way of example, with a bore of about five inches in length, a spring 25 of about eight inches in length is used. In this manner, with the piston 20 inserted the full length of the bore 11, the initial compression of the spring 25 is from about eight inches in length to about five inches, thus establishing an initial precompressed condition for the spring 25.

The handle 30 is then inserted through the opening 18 of the cap 15, and then the threaded end 30a is inserted through the opening 28 of the cup 27. Force is then applied to the handle 30 via the enlarged cap portion 30c to compress the spring 25. It is to be noted that the junction of the shaft 30b and the threaded end 30a forms a shoulder which coacts with the surface of end 27a of cup 27 about the opening 28. Axial force applied to the cap portion 30c of handle 30 results in force applied to the spring retaining cup 27, which is then urged toward the piston member 22 to compress the spring 25 within the bore 11.

After a certain length of compression of the spring 25, the threaded end 30a engages the threaded aperture 20c of piston member 20. The handle 30 is then rotated to tighten the coacting screw portions, thereby completing compression of the spring 25. The flanges 15b of cap member 15 are aligned with the flanges 13 of the bore 11, and screws 17 are then passed through the apertures 16 into threaded engagement with aligned apertures 14, and the screws are tightened to complete the assembly of the syringe 10. The thus assembled syringe 10, with the handle 30 fully inserted and spring 25 fully compressed, is shown in cross-section in FIG. 5. The axial length of the threaded portion 30a is sufficient to enable substantial, or almost full, compression of the spring 25, that is, in the totally compressed state, the adjacent coils of the spring 25 are in abutting or near abutting relation.

Alternatively, the handle 30, cap member 15, cup-shaped retainer 27, spring 25 and piston 20 may be assembled as a unit and then inserted into the bore 11, with the screw members 17 then attaching the cap 15 thereto.

The administration set 40 includes a lockable attachment member, generally designated 42, a length of capillary tubing 50 and a dispensing fitting, generally designated 55. By reference to FIG. 5, the attachment member 42 includes a cup-shaped member 43 having a bottom with an axially aligned externally directed spout 44 with an aperture therethrough in fluid communication with a disc-shaped filter member 45 affixed within the bottom of the cup, the filter 45 having another oppositely directed axially extending tubular portion 46 adapted to be received within the annular opening between sleeve 19b and spout 19a of fitting 19. As a practical matter, as shown in FIG. 2, the disc portion of the filter member 45 serves as the bottom of the cup-shaped member 43. Referring also to FIG. 4, the distal end of tubular portion 46 is provided with outwardly extending diametrically opposed tabs 47, configured for threadable coaction with the double thread screw 19c within sleeve 19b of fitting 19. Locking engagement between the syringe 10 and the administration set 40 is effected, in part, by the engagement of the tabs 47 with the screw 19c.

Additional interlocking engagement is accomplished by the configuration of the cup-shaped member 43, which is provided with an annular inwardly extending shoulder 48 on the interior surface of the member 43 in proximity to the open end thereof, the shoulder 48 being configured and dimensioned for coaction with the annular groove 11a on the exterior of the bore 11. To enable attachment of the set 40, the inner diameter of the cup-shaped member 43 is approximately the same as the outer diameter of the bore 11. The peripheral wall of the cup-shaped member is slotted, that is, it is provided with axially extending slots 49 to enable outward deflection of the arcuate segments when member 43 is fitted to the end of the bore 11.

By reference to FIG. 5, the interconnection or interlocking of the syringe 10 to the administration set 40 will be described. The cup-shaped member 43 is configured so that, upon attachment, and twisting about a quarter turn, the tabs 47 coact with the screw 19c, with the inner annular shoulder 48 of member 43 engaging the annular groove 11a of bore 11. The tubular portion 46 fits snugly and in fluid sealing relation within the annular opening between sleeve 19b and spout 19a of fitting 19. Fluid flow from syringe 10 is then from the interior of bore 11 through the spout 19a, through the filter member 45 and out through spout 44 into the tubing 50, the tubing 50 having a fitting 51 for connection to the spout 44. In actual practice, it is preferable that the filter member 45 be bonded within the cup-shaped member 43, with the fitting 51 bonded to the spout 44, that is the administration set 40 is constructed as an inseparable unit to preserve the integrity of the apparatus as will become apparent. The flow control rate for the infusion apparatus is dictated by the size of the orifice of fitting 51, capillary tubing 50 and fitting 55, or any of them. Thus, a different desired flow rate will require a different administration set 40.

The opposite end of the tubing 50 is provided with the dispensing fitting 55, which is shown in enlarged fragmentary view in FIG. 6, which is configured and adapted for providing a controlled flow of the solution within the syringe 10. For this purpose, the fitting 55 is generally cylindrical or formed as a sleeve with an open end 56. At the other end of the dispensing fitting 55, the tubing 50 is connected thereto to permit fluid flow into the volumetric space within the sleeve of fitting 55. A fluid flow control member 57 is coaxially fitted within the sleeve of fitting 55, the member 57 being a glass or stainless steel tubular member of a short length and of a known internal diameter, the internal diameter providing a metering orifice for controlling the flow rate. One end of this tubular control member 57 is bonded to the interior of the fitting 55 in axial alignment with, and in fluid flow relation with, the tubing 50. For different fluid flow rates, other flow control members 57 are provided with different internal diameters, each of which produces a predictable and/or known flow rate. The syringe 10 may be selectively coupled to one of a number of different administration sets 40, each of which is color coded, with the color code being indicative of a particular fluid flow rate determined by the particular size of the inner diameter of the flow rate control member 57.

As shown in FIG. 6, the distal or free end of control member 57 terminates within the sleeve of fitting 55 a distance from the opening 56. A fluid diffuser member 58 fills the space between the open end 56 and the distal end of the fluid flow control member 57. In practice, the diffuser member 58 is formed of filter or sponge material, of a given length, which has the characteristic of being able to diffuse the stream of fluid from the control member 57. With this material, the distal end of the rigid control member 57 partially enters the center of the adjacent surface of the diffuser member 58, so that solution emanating from the opening 56 exits as a slow stream or drops. In other words, as fluid flows into the diffuser member 58, the member 58 serves to disperse the fluid through the sponge-like interior thereof, causing a dispersal of a slower stream or drops of the solution or fluid through the open end 56.

FIG. 7 shows an alternate interconnection and interlocking arrangement between the syringe 10 and the administration set 40, wherein the periphery of the bore 11 intermediate the annular groove 11a and the end 12 is provided with serrations 60, which coact with mating serrations 62 formed on the interior of the wall of the cup-shaped member 43 below the annular shoulder 48 therein. The serrations 60 and 62 are formed to have an orientation which acts as a ratchet connection, that is, turning in one direction is allowed, with turning in the opposite direction inhibited. The fitting 19 is otherwise the same, along with the coacting tubular portion 46 of member 43. For attachment, the cup-shaped member 43 is placed over the end of bore 11, and turned, with the tabs 47 engaging the thread 19c, while the coacting serrations 60 and 62 permit turning in the direction of the thread 19c. Reversal and thus removal is deterred by both the shoulder 48 and groove 11a fit, as well as the coaction of the serrations 60, 62.

In hospital use, the syringe 10 will be filled by a pharmacist, and the appropriate administration set 40 for the desired flow rate will be attached by the pharmacist. A small amount of fluid or solution will be discharged from the bore 11 by the pharmacist to fill the tubing 50 and the infusion apparatus will then be delivered to the nurse for the particular patient. With the locking means thus provided by either the first interconnection of FIG. 1, or the alternate interconnection of FIG. 7, once the apparatus is filled by the pharmacist, administration of the solution to the patient is straightforward.

For use, to fill the syringe 10 with solution, as shown in FIG. 8, a needle assembly 70 is attached to the funnel-shaped end 12 via nozzle 19a and sleeve 19b. As shown, the spring 25 is fully compressed within bore 11. The needle of the needle assembly 70 is inserted through the septum of a container 72 of the desired solution, whereupon the handle 30 of the syringe 10 is retracted or withdrawn, as indicated by the arrow thereon, and liquid from the container 72 is drawn into the fluid receiving chamber within bore 11, this chamber being the volume between the nose 20a of piston 20 and the interior tapered surface of the funnel-shaped end 12. As shown, the external surface of the bore 11 is suitably calibrated to permit withdrawal of the correct volume of solution from the container 72, with a slight extra volume to compensate for the amount of solution which will be received within the tubing 50 of the administration set 40.

The needle assembly 70 is then removed and discarded. The proper administration set 40 for the desired flow rate is then selected and interconnected to, and interlocked with, the syringe 10 as previously described. The pharmacist then, with the spring 25 still fully compressed as shown in FIGS. 5 and 8, primes the set, that is, the pharmacist discharges a certain amount of the solution from within the syringe 10 by depressing the handle 30, until drops of solution start emanating from the open end 56 of the dispensing fitting 55. A tubing pinch clamp 59, positioned on the tubing 50 is then actuated to its clamped position to secure the unit, and prevent further fluid flow. The fitting 55 is then capped with a cap member 74 (See FIGS. 1 and 5), and the handle 30 is removed by the pharmacist.

The syringe 10 is activated by removal of the handle 30. The handle 30 is rotated in the direction opposite the attaching direction, that is, it is unthreaded from the threaded opening 20c of the piston 20. As the handle 30 is unthreaded, the spring 25 begins to expand, until, at a certain point, the handle 30 is fully unthreaded. The spring retaining cup 27 then starts to spatially separate from the piston 20 within the bore 11 under force of the spring 25. The handle 30 may then be fully removed from the syringe 10. Expansion of the spring 25 continues, with the interference fit between the flared skirt 27a and the interior of bore 11 inhibiting sudden expansion of the spring 25. Finally, the spring 25 is fully expanded with the outer surface of the cup 27 within the bore of the cap member 15 as shown in FIG. 9.

After the syringe 10 is fully activated the apparatus is delivered to the nurse or physician for use. By reference to FIG. 9, the cap 74 is then removed and discarded, and the dispensing fitting 55 is suitably attached to the patient's catheter 77, such as by use of an injection site 78. The tubing pinch clamp 59 is then released to permit flow of solution. Upon release of clamp 59, the force of the spring 25 then urges the relatively incompressible solution within bore 11 toward the funnel shaped end 12 for discharge through the dispensing fitting 55 of the administration set 40, in droplets, at a flow control rate determined by the preselected administration set 40, with a flow control member 57 of predetermined internal dimension.

In accordance with the present invention, there has been shown and described an infusion apparatus, including a syringe 10, with self-contained internal power means for effecting discharge of solution therefrom, with flow rate being controlled by means of selection of one of a plurality of administration sets having inseparable parts, with means provided for interlocking the syringe 10 and selected administration set 40 to preserve the integrity of the apparatus subsequent to filling and prior to use for the administration of drug solutions or the like to a patient. With the configuration of the nose 20a of the piston 20 conforming to the internal taper of the funnel-shaped portion 12, full discharge of the solution may be effected. With the exception of the spring 25, all parts may be conveniently formed or molded from suitable medical grade plastic or Teflon material, and the syringe 10 and administration set 40 may be discarded after use.

While there has been shown and described a preferred embodiment of a disposable infusion apparatus, it is to be understood that various other adaptations and modifications may be made within the spirit and scope of the invention.

I claim:

1. Infusion apparatus for enabling administration of solution to a patient at a controlled flow rate, said apparatus comprising:
    syringe means having bore means configured for receiving solution therein and aperture means adjacent an end thereof, said syringe means including piston means movable within said bore means and defining a solution receiving chamber intermediate said piston means and said aperture means;
    separable handle means configured for coacting engagement with said piston means, said handle means, when coactingly engaging said piston means enabling manual operation of said syringe means for drawing solution into said chamber through said aperture means;
    power means within said bore means intermediate said piston means and the end of said bore means opposite said aperture means, said power means and said handle means being configured for storing energy in said power means on coacting engagement of said handle means with said piston means, and for releasing of the energy upon separation of said handle means from said piston means;
    solution administration means, including solution flow means, at least one of said aperture means and said solution flow means including flow restricting means for controlling the rate of flow of solution therethrough; and
    means for coupling said administration means to said syringe means in fluid flow relation with said aperture means for enabling controllable flow of solution from said chamber through said solution flow means under force of said power means with said handle means separated from said piston means.

2. The infusion apparatus according to claim 1 wherein said power means includes spring means.

3. The infusion apparatus according to claim 2 wherein said coupling means includes means for interlocking said administration means to said syringe means to deter separation.

4. The infusion apparatus according to claim 1 wherein said aperture means includes a spout member and said coupling means includes means for coactingly engaging said spout member.

5. The infusion apparatus according to claim 4 wherein said bore means has a cylindrical outer surface adjacent said spout member, and said coupling means includes a cup member configured for frictionally engaging said outer surface.

6. The infusion apparatus according to claim 5 wherein said cup member has a peripheral skirt portion and the inner wall of said skirt portion and said outer surface include coactingly engaging interlock means.

7. The infusion apparatus according to claim 6 wherein said interlock means includes annular groove means formed on one of said outer surface and said inner wall, and coacting shoulder means formed on the other of said outer surface and inner wall.

8. The infusion apparatus according to claim 7 wherein said annular groove means are formed on said outer surface.

9. The infusion apparatus according to claim 6 wherein said interlock means includes coacting serrations formed on said outer surface and said inner wall.

10. The infusion apparatus according to claim 9 wherein said aperture means includes a spout member and said coupling means includes means for coactingly engaging said spout member by twisting in a given direction, and said serrations are configured and dimensioned for enabling relative movement in said given direction and deterring twisting in the opposite direction.

11. Infusion apparatus for enabling administration of solution to a patient at a controlled flow rate, said apparatus comprising:
  syringe means having a cylindrical bore means with first and second ends;
  aperture means adjacent said first end;
  piston means insertable into and movable within said bore means and defining a solution receiving chamber intermediate said piston means and said aperture means;
  separable handle means having a main shaft portion and a reduced diameter portion having a distal end;
  coacting means formed on the distal end of said reduced diameter portion and on said piston means configured for enabling said handle means to be attached to and separated from said piston means through said second end of said bore means, said handle means, when coactingly engaging said piston means enabling manual operation of said syringe means for drawing solution into said chamber through said aperture means;
  spring means insertable within said bore means intermediate said piston means and the second end of said bore means;
  other means coacting with said spring means and said handle means for enabling compression of said spring means between said piston means and said other means upon attachment of said handle means to said piston means for storage of energy in said spring means, and for enabling manual operation of said syringe means for drawing solution into said chamber through said aperture means;
  solution administration means, including solution flow means, at least one of said aperture means and said solution flow means including flow restricting means for controlling the rate of flow of solution therethrough; and
  means for coupling said administration means to said syringe means in fluid flow relation with said aperture means for enabling controllable flow of solution from said chamber through said fluid flow means under force of said spring means with said handle means separated from said piston means.

12. The infusion apparatus according to claim 11 wherein said coupling means includes means for interlocking said administration means to said syringe means.

13. The infusion apparatus according to claim 11 wherein said solution administration means includes capillary tubing and a dispensing fitting means.

14. The infusion apparatus according to claim 13 wherein said solution flow means are in said dispensing fitting means and includes said flow restricting means and means for diffusing the flow of solution from said restricting means.

15. The infusion apparatus according to claim 12 wherein said aperture means includes a spout member and said coupling means includes a cup member, and wherein said interlocking means includes coacting interengaging means on said cup member and said spout member.

16. The infusion apparatus according to claim 15 wherein said bore means has a cylindrical outer surface adjacent said spout member, and said coupling means includes a cup member configured for frictionally engaging said outer surface.

17. The infusion apparatus according to claim 16 wherein said cup member has a peripheral skirt portion and said interlocking means includes coactingly engaging means formed on the inner wall of said skirt portion and said outer surface.

18. The infusion apparatus according to claim 17 wherein said coactingly engaging means includes annular groove means formed on one of said outer surface and said inner wall, and coacting shoulder means formed on the other of said outer surface and inner wall.

19. The infusion apparatus according to claim 18 wherein said annular groove means are formed on said outer surface.

20. The infusion apparatus according to claim 18 wherein said interlocking means includes coacting serrations formed on said outer surface and said inner wall.

21. The infusion apparatus according to claim 19 wherein said coacting interengaging means on said cup member and said spout member engage by twisting in a given direction, and said serrations are configured and dimensioned for enabling relative movement in said given direction and deterring twisting in the opposite direction.

22. The infusion apparatus according to claim 11 wherein said apparatus further includes a cap member for closing the other end of said bore means, and said other means includes a spring means retaining cup member, and wherein said cap member includes an opening for receiving said main shaft portion therethrough, and wherein said cup member includes an axially aligned opening for receiving said reduced diameter portion of said handle means therethrough.

23. The infusion apparatus according to claim 22 wherein said spring means retaining cup member includes a peripheral skirt portion for frictionally engaging the interior of said bore means.

24. A method for administering solution to a patient through tubing of an administration set having a fluid flow path of predetermined dimensions therethrough and a dispensing fitting, said method comprising:
  providing syringe means having a spout and a cylindrical bore with a movable piston therein for defining a solution receiving chamber intermediate said piston and said spout;
  providing spring means within said bore;
  providing separable handle means configured for coacting engagement with said piston, said handle means, when coactingly engaging said piston compressing said spring means and enabling manual operation of said syringe means for drawing solution into said chamber through said spout;
  manually actuating said piston via said handle means for drawing solution into said chamber;
  attaching the administration set to said spout;
  actuating said handle means to discharge solution from said chamber in a volume at least sufficient to cause flow of solution from said fitting; and
  uncoupling said handle means from engagement with said piston for enabling expansion of said spring means within said bore for urging said piston toward said spout for enabling flow of solution from within said chamber through the fluid flow path of the administration set and through said dispensing fitting.

25. The method according to claim 24 including the further steps of clamping the tubing to stop the flow of solution therethrough, coupling said fitting to other means in fluid communication with a patient, and unclamping said tubing to permit flow of solution to the patient.

26. The method according to claim 24 further including the steps of attaching needle means to said spout prior to actuating said piston via said handle means for drawing solution into said chamber and removing said needle means prior to attaching the administration set to said spout.

27. The method according to claim 26 wherein the step of attaching the administration set to said spout includes interlocking the administration set to said spout.

28. Infusion apparatus for enabling administration of solution to a patient at a controlled flow rate, said apparatus comprising:
    syringe means having:
        bore means configured for receiving solution therein and aperture means adjacent an end thereof,
        piston means movable within said bore means and defining a solution receiving chamber intermediate said piston means and said aperture means;
    separable handle means configured for coacting engagement with said piston means, said handle means, when coactingly engaging said piston means enabling manual operation of said syringe means for drawing solution into said chamber through said aperture means;
    power means within said bore means intermediate said piston means and the end of said bore means opposite said aperture means, said power means and said handle means being configured for storing energy in said power means on coacting engagement of said handle means with said piston means, and for releasing of the energy upon separation of said handle means from said piston means;
    a plurality of sets of solution administration means, each of said sets including:
        solution flow means; and
        means for coupling said administration means to said syringe means in fluid flow relation with said aperture means for enabling flow of solution from said chamber through said solution flow means under force of said power means with said handle means separated from said piston means, the solution flow means of each of said sets having flow restricting means of different dimensions for enabling selection of a given set for a desired rate of flow of solution therethrough.

29. The infusion apparatus according to claim 28 wherein said power means includes spring means.

30. The infusion apparatus according to claim 28 wherein said coupling means includes means for interlocking said administration means to said syringe means to deter separation.

31. The infusion apparatus according to claim 28 wherein said aperture means includes a spout member and said coupling means includes means for coactingly engaging said spout member.

32. The infusion apparatus according to claim 31 wherein said bore means has a cylindrical outer surface adjacent said spout member, and said coupling means includes a cup member configured for frictionally engaging said outer surface.

33. The infusion apparatus according to claim 32 wherein said cup member has a peripheral skirt portion and the inner wall of said skirt portion and said outer surface include coactingly engaging interlock means.

34. The infusion apparatus according to claim 33 wherein said interlock means includes annular groove means formed on one of said outer surface and said inner wall, and coacting shoulder means formed on the other of said outer surface and inner wall.

35. The infusion apparatus according to claim 34 wherein said annular groove means are formed on said outer surface.

36. The infusion apparatus according to claim 33 wherein said interlock means includes coacting serrations formed on said outer surface and said inner wall.

37. The infusion apparatus according to claim 36 wherein said aperture means includes a spout member and said coupling means includes means for coactingly engaging said spout member by twisting in a given direction, and said serrations are configured and dimensioned for enabling relative movement in said given direction and deterring twisting in the opposite direction.

38. Infusion apparatus for enabling administration of solution to a patient at a controlled flow rate, said apparatus comprising:
    syringe means having bore means configured for receiving solution therein and aperture means adjacent an end thereof, said syringe means including piston means movable within said bore means and defining a solution receiving chamber intermediate said piston means and said aperture means;
    handle means configured for separable coacting engagement with said piston means, said handle means, when coactingly engaging said piston means enabling manual operation of said syringe means for drawing solution into said chamber through said aperture means;
    power means within said bore means intermediate said piston means and the end of said bore means opposite said aperture means, said power means and said handle means being configured for storing energy in said power means on coacting engagement of said handle means with said piston means, and for releasing of the energy upon separation of said handle means from said piston means; and
    means connectable to said syringe means in fluid flow relation with said aperture means for enabling flow of solution from said chamber to a patient under force of said power means with said handle means separated from said piston means.

39. Infusion apparatus according to claim 38 wherein one of said aperture means and said means connectable to said syringe means includes flow restricting means for controlling the rate of flow of solution from said chamber.

40. The infusion apparatus according to claim 39 wherein said means connectable to said syringe means includes cup means connectable to said bore means adjacent said aperture means.

41. The infusion apparatus according to claim 39 wherein said means connectable to said syringe means includes means for coactingly engaging said bore means adjacent said aperture means.

42. The infusion apparatus according to claim 41 wherein said coactingly engaging means includes interlock means for deterring separation of said syringe means from said means connectable to said syringe means.

43. The infusion apparatus according to claim 38 wherein said power means includes spring means insertable within said bore means intermediate said piston means and the end of said bore means opposite said aperture means, and other means coacting with said spring means and said handle means for enabling compression of said spring means between said piston means and said other means upon attachment of said handle means to said piston means.

44. The infusion apparatus according to claim 43 wherein said handle means includes a main shaft portion and a reduced diameter portion and wherein said apparatus further includes a cap member for closing the other end of said bore means, and wherein said other means includes a spring means retaining cup member, and wherein said cap member includes an opening for receiving said main shaft portion therethrough, and wherein said cup member includes an axially aligned opening for receiving said reduced diameter portions of said handle means therethrough.

45. The infusion apparatus according to claim 44 wherein said spring means retaining cup member includes a peripheral skirt portion for frictionally enjoying the interior of said bore means.

* * * * *